(12) United States Patent
Aljizawi (10) Patent No.: US 8,221,453 B2
(45) Date of Patent: Jul. 17, 2012

(54) LAPAROSCOPIC AUTO-KNOT SUTURES DEVICE

(76) Inventor: Hakim Mahmoud Aljizawi, Arcadia, CA (US)

( * ) Notice: Subject to any disclaimer, the term of this patent is extended or adjusted under 35 U.S.C. 154(b) by 749 days.

(21) Appl. No.: 12/070,349

(22) Filed: Feb. 16, 2008

(65) Prior Publication Data

US 2009/0209981 A1  Aug. 20, 2009

(51) Int. Cl.
*A61B 17/04* (2006.01)
*A61B 17/06* (2006.01)
(52) U.S. Cl. ........................................ 606/232; 606/222
(58) Field of Classification Search ................. 606/139, 606/222, 232; 289/17; 24/15
See application file for complete search history.

(56) References Cited

U.S. PATENT DOCUMENTS

| 4,373,532 | A | * | 2/1983 | Hill et al. | 600/458 |
| 5,527,341 | A | * | 6/1996 | Gogolewski et al. | 606/232 |
| 5,735,875 | A | * | 4/1998 | Bonutti et al. | 606/232 |
| 5,984,933 | A | * | 11/1999 | Yoon | 606/232 |

\* cited by examiner

*Primary Examiner* — Corrine M McDermott
*Assistant Examiner* — Melissa Ryckman (57) ABSTRACT

A surgical knotting device comprising a length of suture thread; a first portion located and held in place on the length of suture thread; a needle on the length of suture thread at a position spaced from where the first portion is located; a second portion attached to the first portion and having a groove therein adapted to receive the length of suture thread at a point between where the first portion is located and the needle, and to secure the length of suture thread in place; and an auxiliary thread on the length of suture thread at an end opposite the needle.

6 Claims, 9 Drawing Sheets

LAPAROSCOPIC AUTO-KNOT SUTURES DEVICE

BACKGROUND OF THE INVENTION

Laparoscopic suturing and knot tying are considered the most difficult laparoscopic skill to master. Many surgeons find difficulties in making knots after suturing due to limited space during laparoscopic surgery and since it is a technically demanding part of the procedure, in addition to the time needed to make such knots, most surgeons require training courses to be able to perform laparoscopic knots. The learning curve requires performing many operations before a surgeon becomes comfortable in mastering these knots. This device will save time with less training.

BRIEF SUMMARY OF THE INVENTION

An easy built-in knotting mechanism (auto-knot device) attached to the auxiliary thread that will allow the device to be adjusted to the proper position to insert the suture thread into the groove and secure the knot by pulling the auxiliary thread and the suture thread in opposite directions to finish the knot. The device is two spheres fused together, one sphere has a groove to secure suture thread and the other one has a knot to keep the device in place a longer period of time during the absorbent stage in case absorbable material has been used. This device will reduce the time required to accomplish the task of laparoscopic suturing and knot tying by requiring only one surgeon to perform the surgery (See FIGS. 7-12), showing, in reduced scale, the steps of making the knot in the tissue using the device and needle holders. It will also make laparoscopic knots feasible for right and left-handed surgeons and with fore-handed and back hand suturing. This device can be used with any size suture thread or any type of suture needle and can be manufactured from any material that is not harmful to the human body.

BRIEF DESCRIPTION OF THE DRAWINGS

The attached sheets of drawings include changes to FIGS. 1-12. These sheets, which include FIGS. 1-12, replace the original sheets including FIGS. 1-12.

DETAILED DESCRIPTION OF THE DRAWINGS

Figure 1:
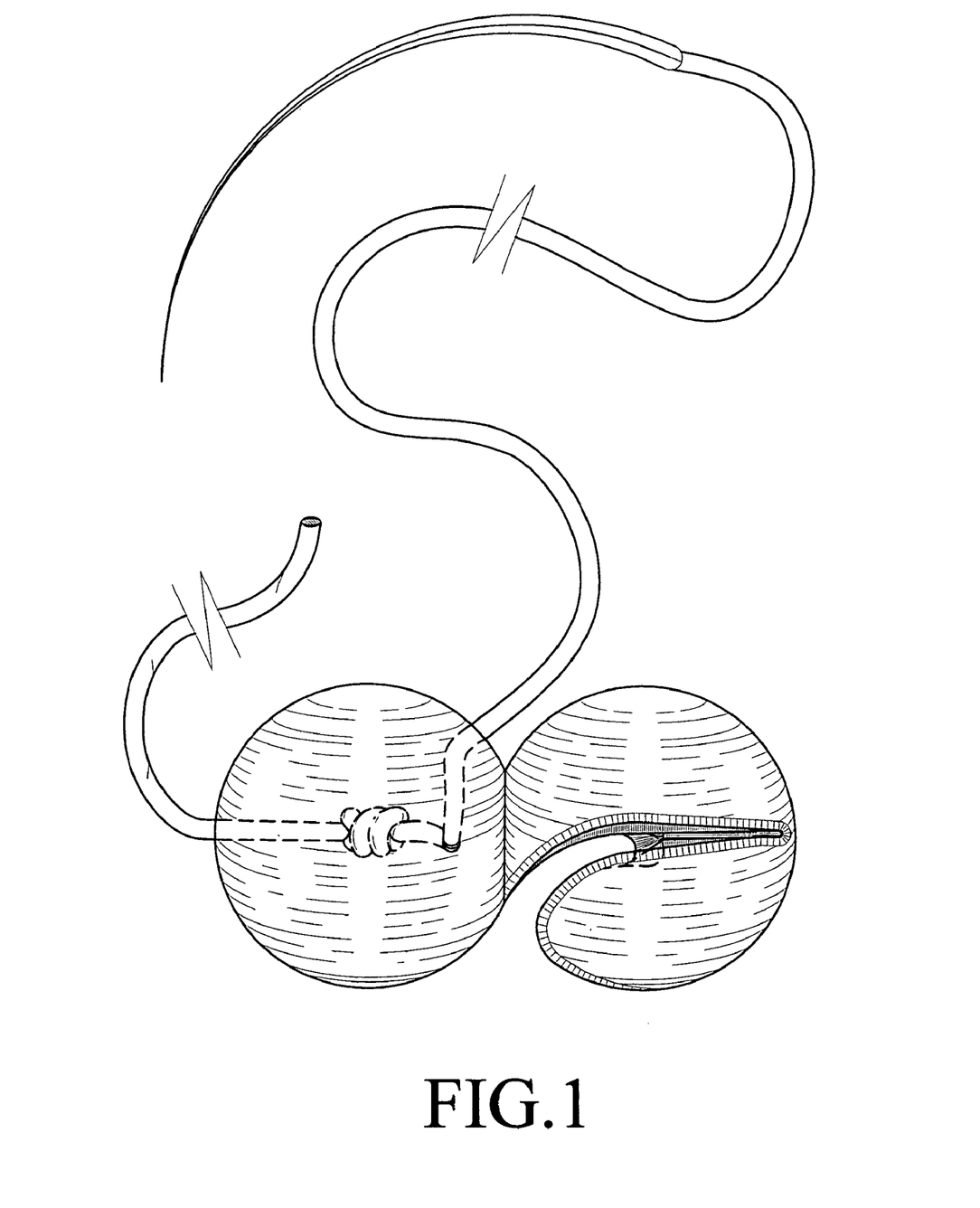
FIG. 1 is a top, front, and right hand side perspective view of the Laparoscopic Suturing Auto-Knot Device.

FIG. 1 is a top, front, and right hand side perspective view of the Laparoscopic Suturing Auto-Knot Device.

Figure 2:
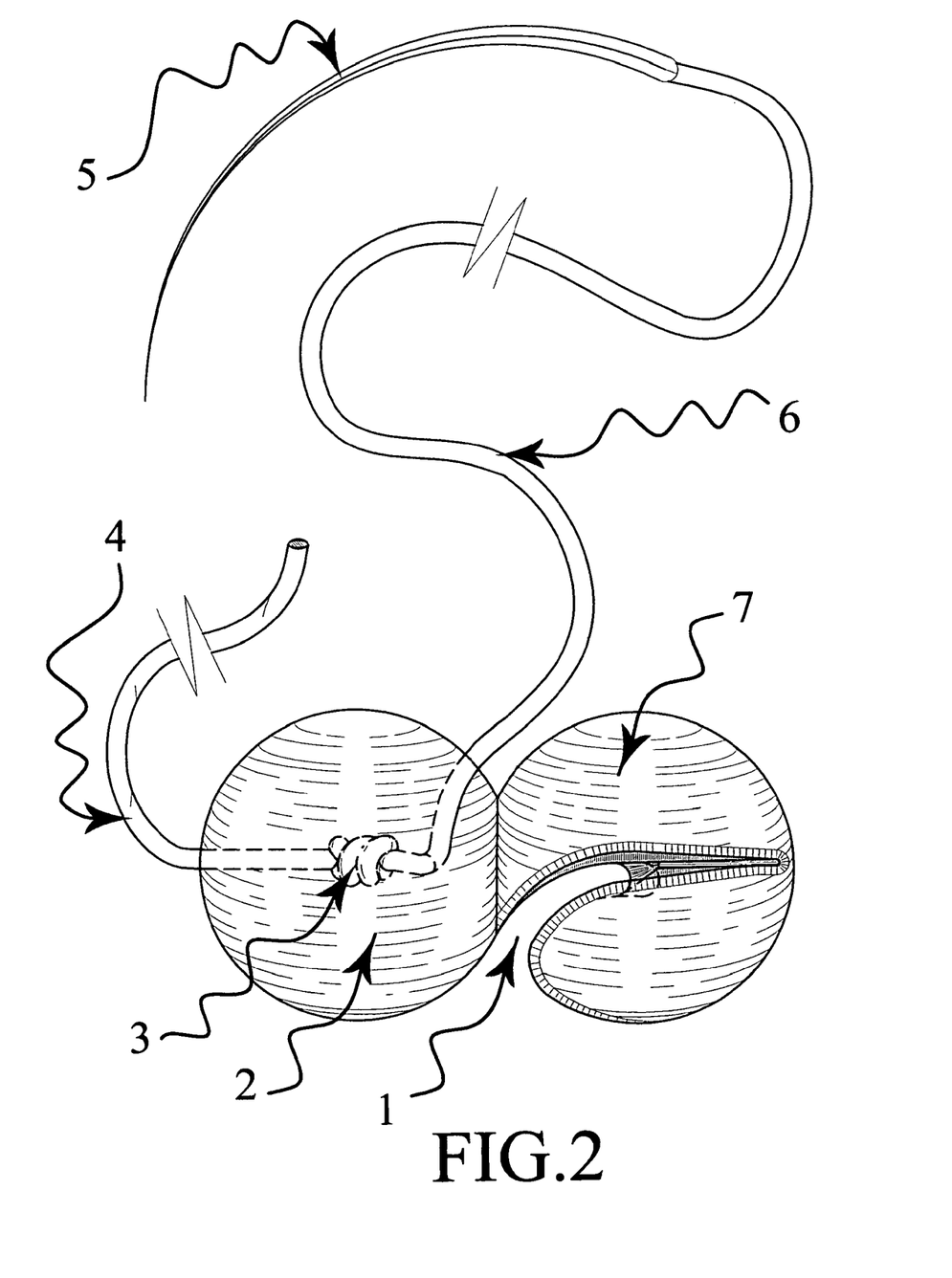
FIG. 2 is the same embodiment as shown in FIG. 1.

FIG. 2 is the same As FIG. 1, but showing reference numbered arrows, 1-7, pointed at the components of the device, which is: 1—Groove; 2—Left-hand Spheres; 3—Knot; 4—Auxiliary thread, 5—Needle; 6—Suture thread; and 7—Right-hand sphere.

Figure 3:
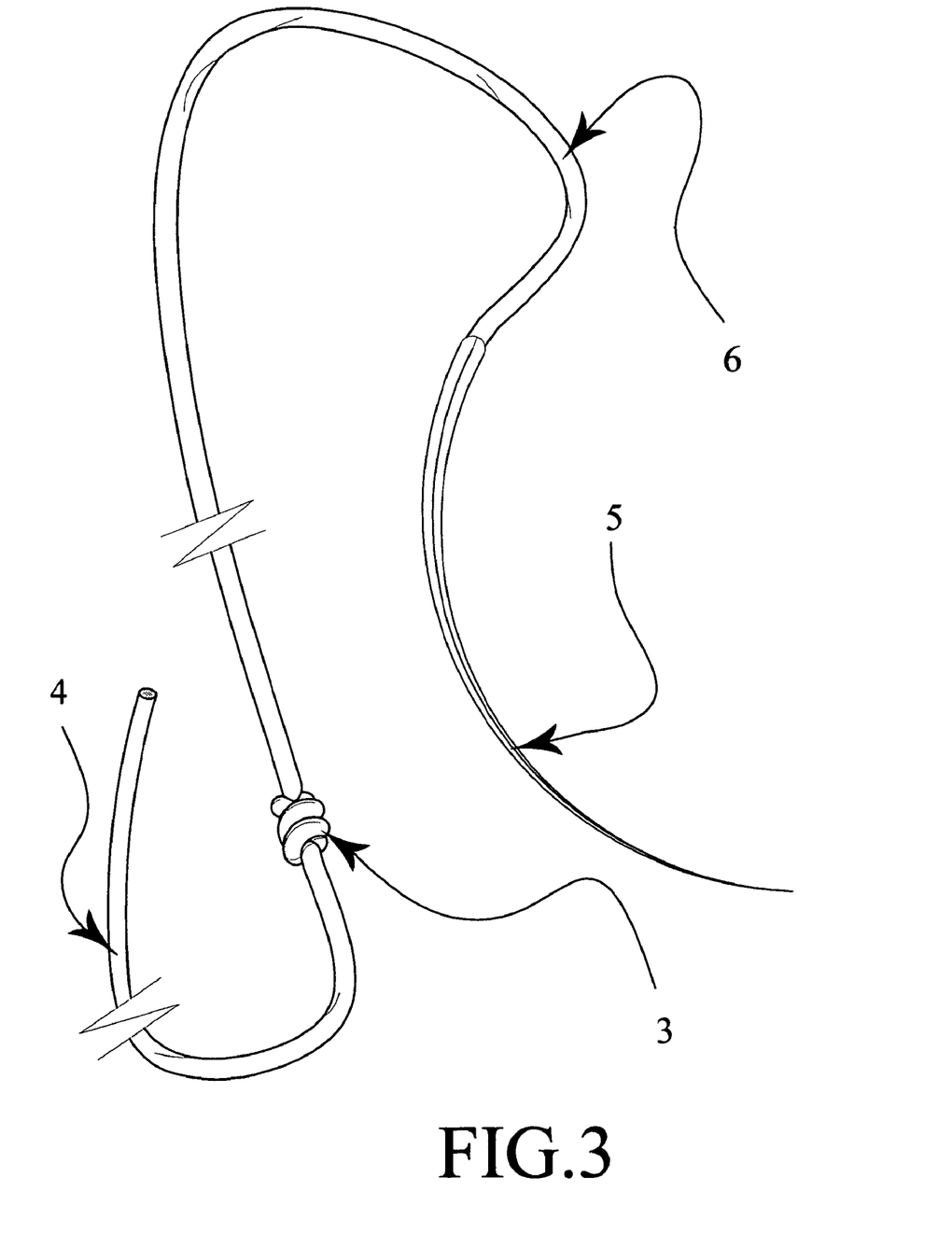
FIG. 3 is a perspective view of the embodiment as shown in FIG. 1.

FIG. 3 is a perspective view of the needle, suture thread, and auxiliary thread with the knot in between, before fusion into device.

Figure 4:
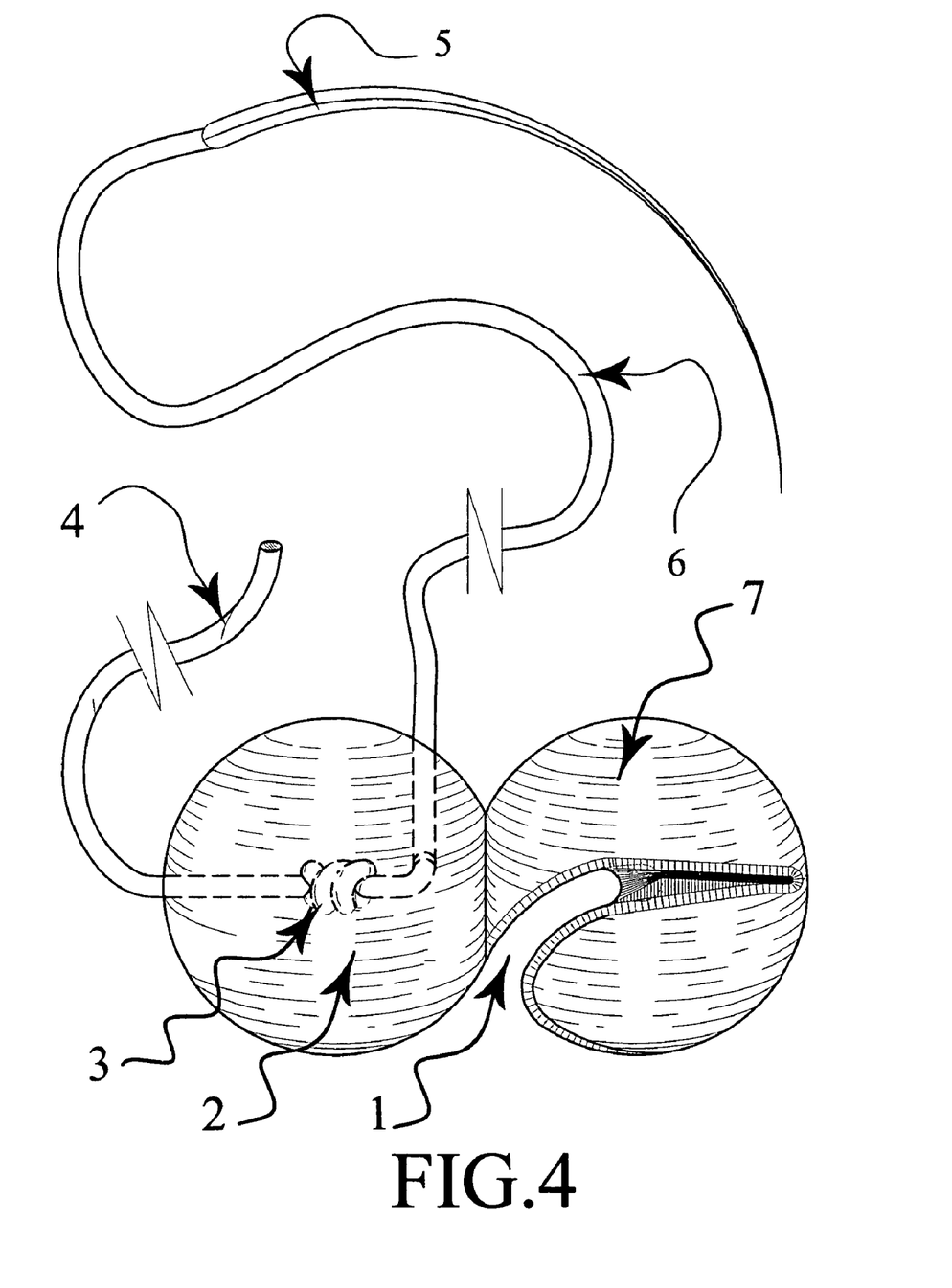
FIG. 4 is a top perspective view of the embodiment as shown in FIG. 1.
Figure 5:
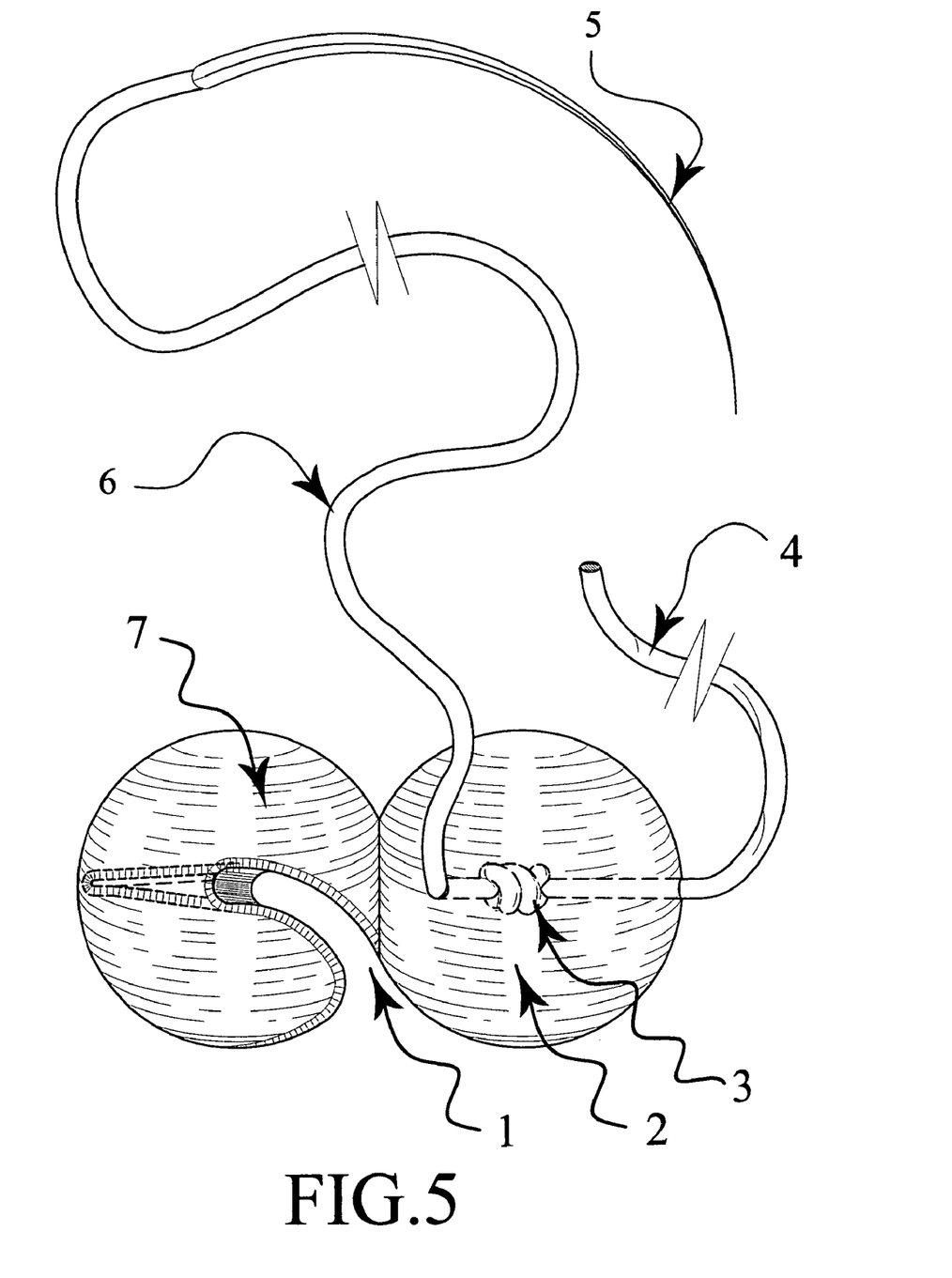
FIG. 5 shows a bottom perspective view of the embodiment as shown in FIG. 1.
Figure 6:
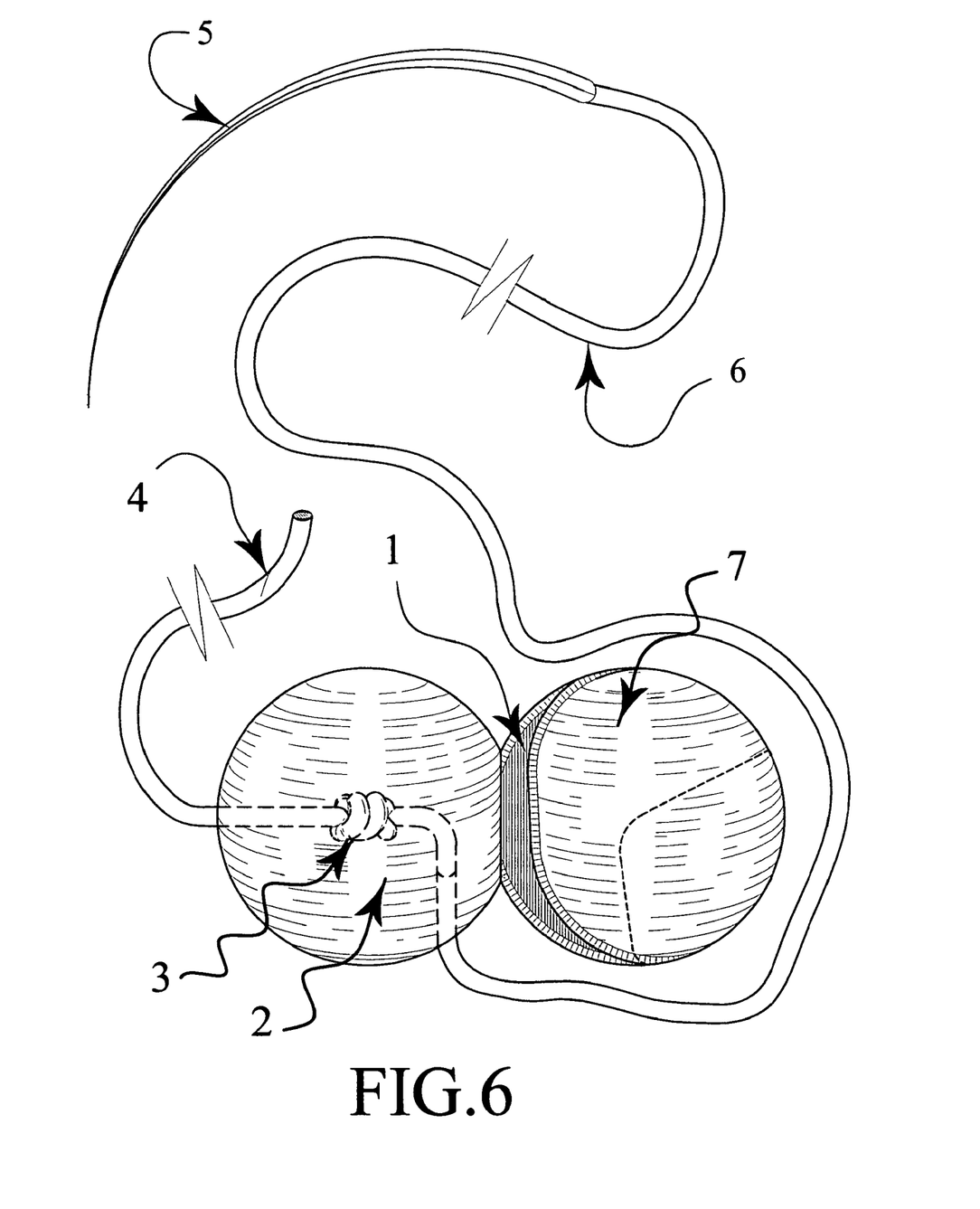
FIG. 6 shows a front perspective view of the embodiment as shown in FIG. 1.
Figure 7:
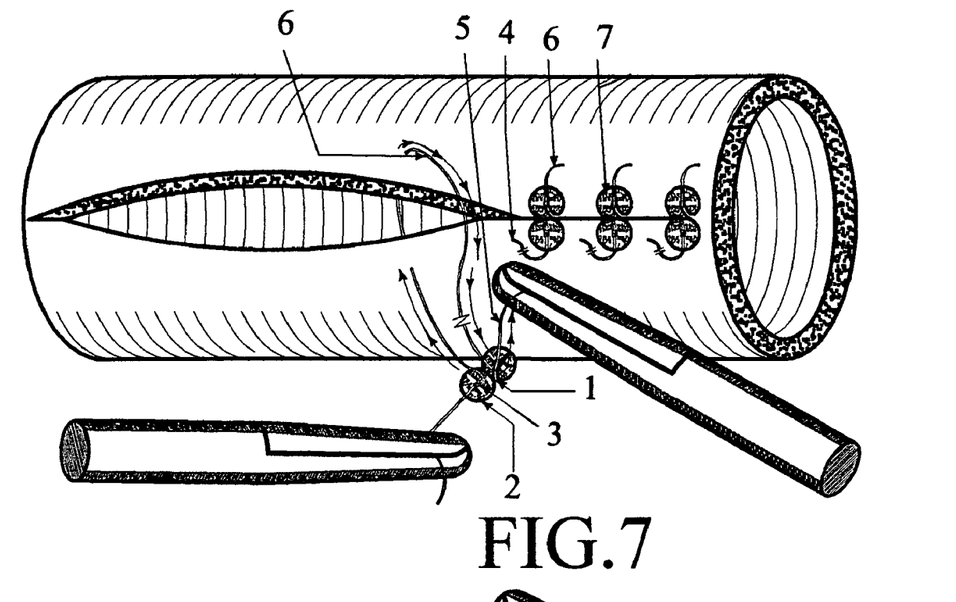
FIG. 7 shows the device in use with tissue.

FIG. 4 is a top perspective view of the device thereof;

FIG. 5 is showing a bottom perspective view thereof;

FIG. 6 shows a front perspective view thereof;

FIG. 7 is a top, front and right hand side perspective view showing direction of the suture thread being passed through the tissue, using two needle holders, one holding the suture thread needle and the other one holding the auxiliary thread in order to complete the knot by pulling the suture thread into the grove of the device.

Figure 8:
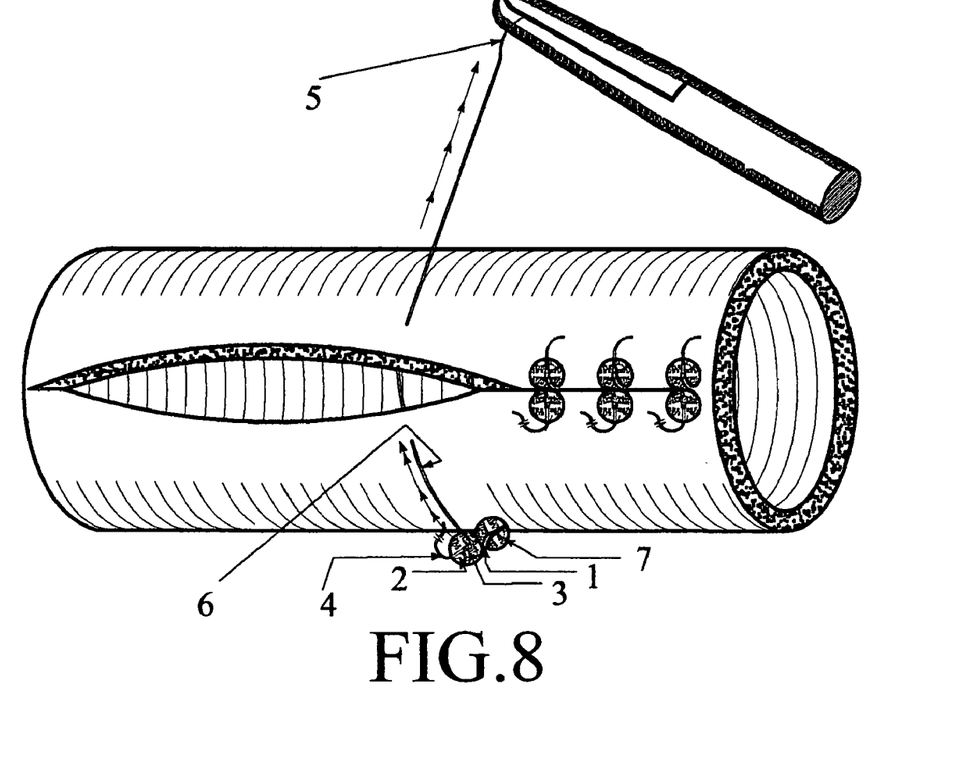
FIG. 8 is a top, front, and right hand side perspective view showing the device in use with tissue.

FIG. 8 is a top, front, and right hand side perspective view showing step 1—of making the knot by showing the suture thread being pulled forward through the tissue in the direction of the arrows in order to put the device in place.

Figure 9:
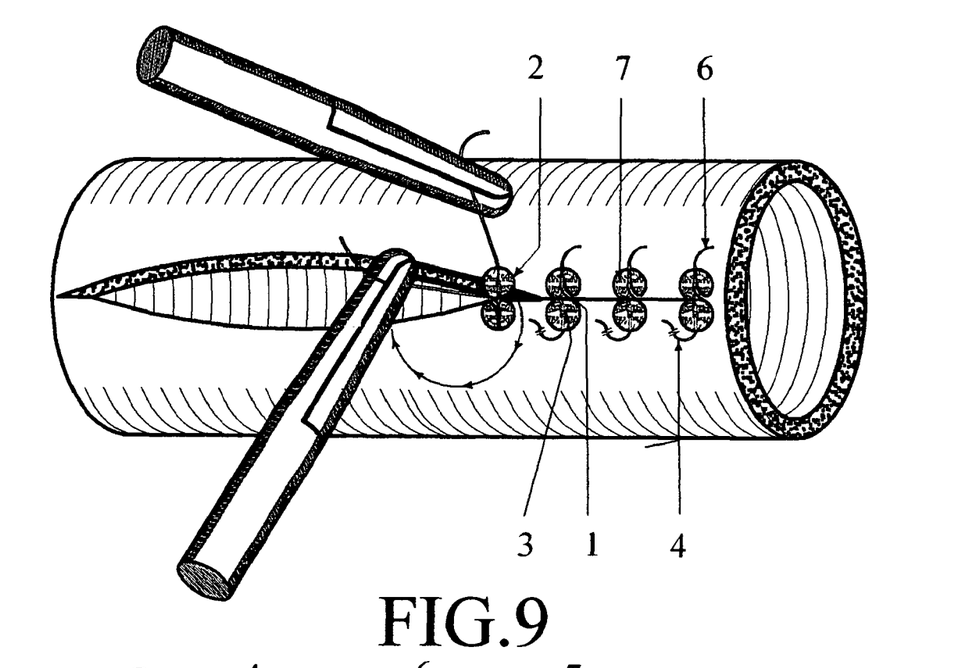
FIG. 9 is a top, front, and right hand side perspective view showing a knot being made.

FIG. 9 is a top, front, and right hand side perspective view showing step 2—of making the knot by showing the suture thread being pulled backwards and the auxiliary thread being pulled forward. Both of them in the direction of the arrows.

Figure 10:
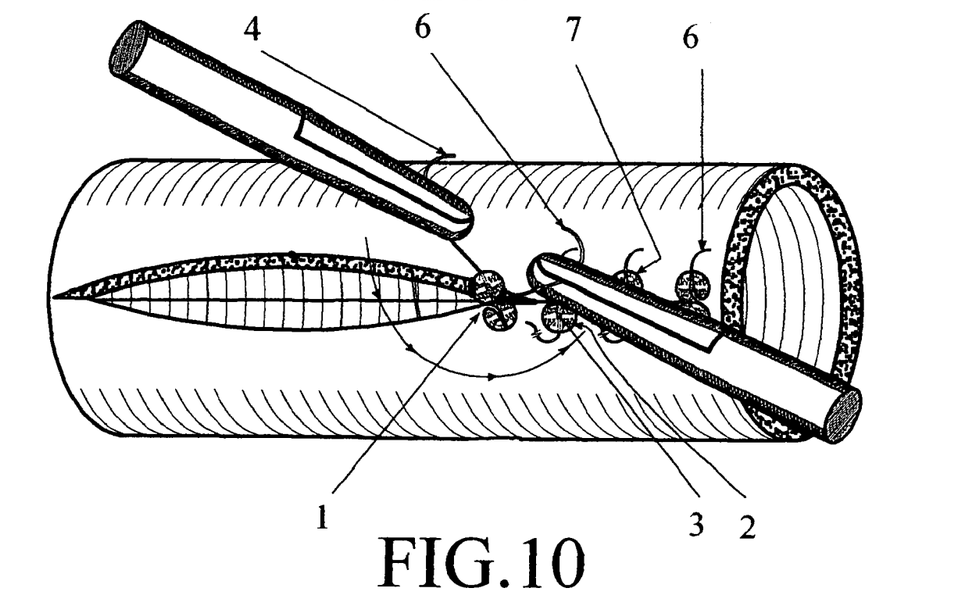
FIG. 10 is a top, front, and right hand side perspective view showing a knot being made.

FIG. 10 is a top, front, and right hand side perspective view showing step 3—of making the knot by showing the suture thread being rotated underneath the device, about 100 degrees clockwise, in order to make the suture thread face the groove.

DETAILED DESCRIPTION OF THE DRAWINGS (CONT'D.)

Figure 11:
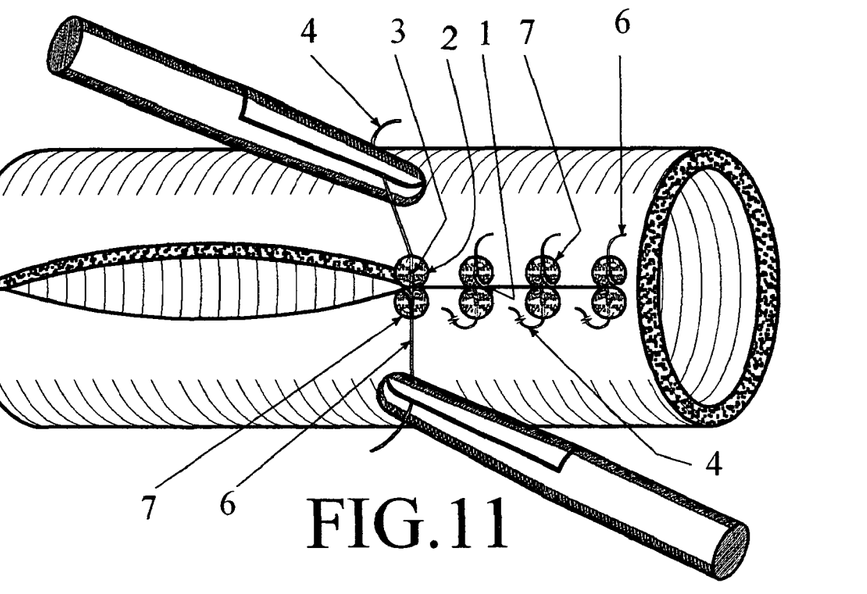

FIG. 11 is a top, front, and right hand side perspective view showing step 4—of making the knot by showing that the suture thread has been pulled up and placed in the groove to start rotating the device counter-clockwise in the direction of the arrows.

Figure 12:
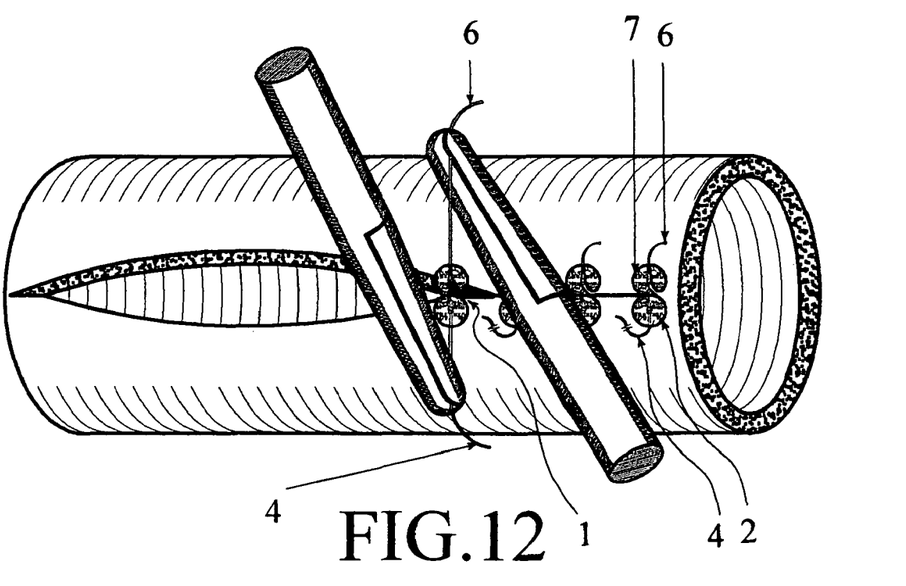

FIG. 12 is a top, front, and right hand side perspective view showing the knot has been put in place and secured, by pulling the suture thread and the auxiliary thread in opposite direction to secure the suture thread at the end of the groove to complete the knot.

The invention claimed is:

1. A laparoscopic suturing knot device comprising:
    a suture thread with a needle;
    an auxiliary thread;
    two spheres fused together at a fused portion wherein a first sphere has a groove extending inwardly from the fused portion for securing the suture thread and a second sphere has an auxiliary thread fused within the second sphere for adjusting the device to a proper position and completing a suture knot.

2. The device of claim 1 wherein the suture thread is fused in the second sphere to keep the device in place.

3. The device of claim 1 wherein the suture thread, the first sphere and the second sphere are made of absorbable material.

4. The device of claim 1 wherein the groove extends into the first sphere and becomes progressively narrower as it extends in the first sphere.

5. The device of claim 1 wherein the auxiliary thread is on the length of suture thread at an end opposite the needle.

6. A surgical knotting device comprising:
    a suture thread;
    a first sphere with a portion of the suture thread fused within the first sphere;

a needle at an end of the suture thread at a position spaced from the first sphere;

a second sphere attached to the first sphere forming an attachment region and having a groove extending inwardly from the attachment region, the groove is adapted to receive the suture thread at a point between the first sphere and the needle, the groove secures the suture thread in place; and an auxiliary thread on the suture thread, at an end opposite the needle, adapted to adjust the device and complete a knot.

* * * * *